United States Patent
Shin et al.

(10) Patent No.: US 10,473,600 B2
(45) Date of Patent: Nov. 12, 2019

(54) SELECTIVE NMR PULSE FOR DOWNHOLE MEASUREMENTS

(71) Applicant: Halliburton Energy Services, Inc., Houston, TX (US)

(72) Inventors: Chang S. Shin, Kingwood, TX (US); Paul Joseph Ganssle, Houston, TX (US); Shriram Sarvotham, Houston, TX (US); Songhua Chen, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 107 days.

(21) Appl. No.: 15/305,540

(22) PCT Filed: Dec. 22, 2015

(86) PCT No.: PCT/US2015/067266
§ 371 (c)(1),
(2) Date: Oct. 20, 2016

(87) PCT Pub. No.: WO2017/111935
PCT Pub. Date: Jun. 29, 2017

(65) Prior Publication Data
US 2018/0017700 A1    Jan. 18, 2018

(51) Int. Cl.
| | |
|---|---|
| G01N 24/08 | (2006.01) |
| G01R 33/44 | (2006.01) |
| G01V 3/32 | (2006.01) |
| E21B 49/08 | (2006.01) |
| E21B 47/12 | (2012.01) |
| G01R 33/58 | (2006.01) |

(52) U.S. Cl.
CPC ........ *G01N 24/081* (2013.01); *E21B 47/12* (2013.01); *E21B 49/08* (2013.01); *G01R 33/448* (2013.01); *G01V 3/32* (2013.01); *G01R 33/583* (2013.01)

(58) Field of Classification Search
CPC ......... G01V 3/32; G01N 24/081; E21B 49/08
See application file for complete search history.

(56) References Cited

U.S. PATENT DOCUMENTS

| | | |
|---|---|---|
| 6,064,207 A | 5/2000 | Kupce |
| 6,094,049 A | 7/2000 | Rosenfeld et al. |
| 8,324,898 B2 | 12/2012 | Sung et al. |

(Continued)

OTHER PUBLICATIONS

"International Application Serial No. PCT/US2015/067266, International Search Report dated Sep. 21, 2016", 3 pgs.

(Continued)

*Primary Examiner* — Rodney A Bonnette
(74) *Attorney, Agent, or Firm* — Haynes and Boone, LLP

(57) ABSTRACT

Various embodiments include a method for generating a pulse for use in nuclear magnetic resonance (NMR) logging. One such method generates the pulse by adjusting one or more of pulse parameters including a pulse shape, a pulse amplitude, a pulse phase, and/or a pulse frequency. The generated pulse produces a substantially uniform nuclear spin saturation or nuclear spin inversion response from a fluid. A wait time between the pulse transmission and an echo that indicates spin equilibrium has been achieved is substantially equal to a $T_1$ time indicating characteristics of the fluid.

16 Claims, 11 Drawing Sheets

(56) References Cited

U.S. PATENT DOCUMENTS

2003/0071617 A1\* 4/2003 Kruspe .............. G01R 33/4616
 324/303
2004/0257074 A1 12/2004 Appel et al.
2013/0342210 A1\* 12/2013 Stokely ................. G01R 33/26
 324/346

OTHER PUBLICATIONS

"International Application Serial No. PCT/US2015/067266, Written Opinion dated Sep. 21, 2016", 8 pgs.
Alberto, et al., "Adiabatic Pulses", NMR in biomedicine, vol. 10, No. 8, (1997), 423-434.

\* cited by examiner

US 10,473,600 B2

SELECTIVE NMR PULSE FOR DOWNHOLE MEASUREMENTS

RELATED APPLICATIONS

This application is a U.S. National Stage Filing under 35 U.S.C. 371 of International Patent Application Serial No. PCT/US2015/067266, filed Dec. 22, 2015, the benefit of priority of which is claimed hereby and which is incorporated herein by reference in its entirety.

BACKGROUND

Nuclear magnetic resonance (NMR) logging is a type of well logging that uses the NMR response of a formation to determine its porosity and permeability, providing a continuous record along the length of a borehole. NMR logging exploits the magnetic moment of hydrogen, which is abundant in rocks in the form of fluids. The NMR signal amplitude is proportional to the quantity of hydrogen nuclei present in a formation and can be calibrated to give a value for porosity that is free from lithology effects.

NMR logs provide information about the quantities of fluids present, the properties of these fluids, and the sizes of the pores containing these fluids. From this information, it is possible to estimate the volume (porosity) and distribution (permeability) of the rock pore space, the rock composition, the type and quantity of fluid hydrocarbons, as well as the hydrocarbon producibility.

Generally, NMR tools operate by imposing a static magnetic field on a geological formation. This magnetic field is traditionally referred to as the "static field" as it is usually independent of time and is given the symbol $B_0$. A second magnetic field, which varies in time, is also applied. This field is typically designated as $B_1$ and is traditionally called the "radio frequency field". It is turned on and off at different increments, known as a pulse. This second, perturbing field is perpendicular to the static field, $B_0$. The perturbing field moves the magnetization away from the thermal equilibrium. Generating the perturbing field takes a significant amount of energy, which may be in short supply downhole, especially if the logging tool is powered by batteries.

A particular type of energy-consuming RF pulse is a broadband saturation pulse that may commonly be used for downhole NMR logging of the spin-lattice relaxation time ($T_1$) measurements. In a typical logging while drilling (LWD) NMR logging $T_1$ logging sequence, the single broadband saturation chirp pulse uses about 25% more RF energy than an optimal saturation pulse may use. Furthermore, the chirp pulse uses a cumbersome calibration process that is time consuming and affects operation efficiency.

DETAILED DESCRIPTION

Some of the challenges noted above, as well as others, can be addressed by forming an adiabatic saturation or inversion pulse that is generated in terms of bandwidth, selectivity, pulse length, total radio frequency (RF) energy consumption, and/or lower peak RF amplitude based on the logging application. By solving Bloch's equations for a $T_1$ measurement sequence and phase-cycling the $T_1$ measurement sequence, calibration procedures may be simplified and logging quality improved by suppressing undesirable signal contributions. Additionally, pulse parameters (e.g., pulse shape, bandwidth, selectivity, length, phase, frequency, total RF energy consumption, amplitude) may be selectively adjusted, as described subsequently, to increase NMR logging times without increasing energy usage. Solving the technical problem in this way can save energy, contributing to a more efficient NMR measurement process.

As used herein, adiabatic pulses may be defined as amplitude and frequency modulated RF-pulses that are relatively insensitive to $B_1$ inhomogeneity and frequency offset effects. The pulses utilize the adiabatic principle wherein magnetization (M) is manipulated by a slow passage of the $B_1$ field through resonance. With adiabatic pulses, nuclear spins having different resonant frequencies are inverted or manipulated at different times. This differs from a rectangular amplitude modulated (AM) RF-pulse where all nuclear spins are affected substantially simultaneously.

Figure 1:
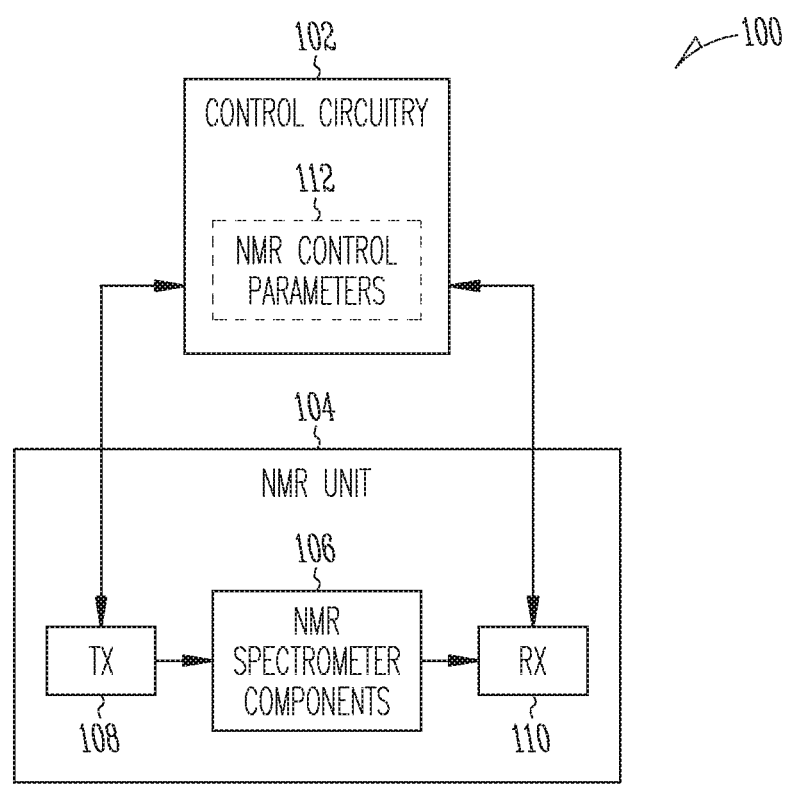
FIG. 1 is a diagram showing an NMR tool, according to various examples of the disclosure.

FIG. 1 is a diagram showing an NMR tool 100, according to various examples of the disclosure. The NMR sensor tool 100 of FIG. 1 is for purposes of illustration only as the various examples disclosed herein may be used in other NMR tools.

The NMR tool 100 includes control circuitry 102 that provides NMR control parameters 112 to an NMR unit 104. In an example, the components of the NMR tool 100 may be located at the surface (e.g., as part of an NMR facility or laboratory) or downhole (e.g., as part of one or more logging tools). In other examples, some of the components (e.g., control circuitry 102) may be located at the surface while other components (e.g., NMR unit 104) are located downhole.

The NMR unit 104 includes a transmitter (TX) 108, a receiver (RX) 110, and NMR spectrometer components 106 for transmitting RF pulses and receiving NMR signals. The transmitter 108 may include, for example, a programmable pulse sequence device, a radio frequency (RF) synthesizer, a phase shifter, a pulse gate, an amplifier, and/or other components. The receiver 110 may include, for example, an analog-to-digital converter (ADC), filters, mixers, splitters, pre-amplifiers, and/or other components to receive magnetic resonance signals and recover measurement data. The magnetic resonance spectrometer components 106 may include one or more magnets, shim coils, probes/antennas, and/or field-frequency lock components. The magnetic resonance spectrometer components 106 may further include a duplexer that enables separation between transmission current and reception current.

The control circuitry 102 directs the operations of the NMR unit 104 (e.g., a downhole tool or laboratory equipment) by providing commands, programming, and/or data to the transmitter 108 of the magnetic resonance unit 104. Further, in some examples, the magnetic resonance control parameters 112 enable adjustment of pulse sequences and receiver window options based on a default configuration, user selection, and/or calibration.

The transmitter 108 of the NMR unit 104 is configured to transmit signals (e.g., modulated saturation pulses). If the NMR unit 104 is part of a downhole tool, the signals are transmitted into a geological formation in order to determine a composition of the formation.

The receiver 110 of the NMR unit 104 is configured to receive and decode magnetic resonance signals (e.g., from a geological formation). If the NMR unit 104 is part of a downhole tool, the received signals may comprise a reflected response from the geological formation (e.g., reservoir, volume to be measured). The raw NMR measurements or processed NMR data is output from the receiver 110 to the control circuitry 102 for storage, display, and/or analysis. In some embodiments, the control circuitry 102 may further process raw NMR measurements or processed NMR data received from the NMR unit 104.

The NMR tool 100 may be used as part of the methods described herein to improve the accuracy and efficiency of the $T_1$ measurement in NMR logging. One aspect of some methods generates a pulse or train of pulses that are shaped (i.e., the pulse parameters are adjusted) in such a way as to realize a saturation or inversion of the z component of the magnetization for the $T_1$ measurement in saturation recovery pulse sequence or inversion recovery pulse sequence, respectively.

The $T_1$ relaxation time is indicative of the characteristics of the geological formation being measured. For example, different types of formation and different types of fluids may result in different $T_1$ relaxation times during an NMR logging operation. Fluids, as used herein, may include liquids or gases.

The generated pulse or train of pulses from the NMR tool 100 may be adiabatic pulses that are shaped (i.e., the pulse parameters are adjusted) to provide a wide frequency bandwidth by using appropriate modulation functions for the AM, frequency modulation (FM) or phase modulation (PM). Such a pulse may use less RF peak amplitude to realize substantially uniform saturation or inversion of the nuclear spins over a wide bandwidth with high selectivity where available peak RF amplitude is limited. This may also extend the total logging time of a logging tool. Thus a saturation or inversion pulse may be considered optimized when it results in a substantially uniform saturation or inversion response from a formation (e.g., fluid) while using a minimum amount of RF energy (i.e., least amount of RF energy), where the minimum amount of RF energy is indicated by the result of Bloch's equations.

Calibration procedures may be used to adjust one or more of the pulse parameters (e.g., bandwidth, selectivity, pulse length, total RF energy consumption, amplitude and duration) of an adiabatic pulse to realize the saturation or inversion of the z component of the magnetization of the nuclear spins. Additionally, phase-cycling techniques may be used to suppress undesirable signals resulting from the gradient of the magnetic field at a bandwidth and inhomogeneity of the $B_1$ field.

Subsequent examples utilize Bloch's equations. As used herein Bloch's equations are a set of macroscopic equations that are used to calculate the nuclear magnetization $M=(M_x, M_y, M_z)$ as a function of time when relaxation times $T_1$ and $T_2$ are present (i.e., $T_1$=nuclear spin-lattice relaxation (relaxation in the z-direction), $T_2$=nuclear spin-spin relaxation (relaxation in the x-y plane)). Bloch's equations are considered macroscopic since they describe the equations of motion of macroscopic nuclear magnetization that can be obtained by summing up all nuclear magnetic moment in the sample.

Figure 2:
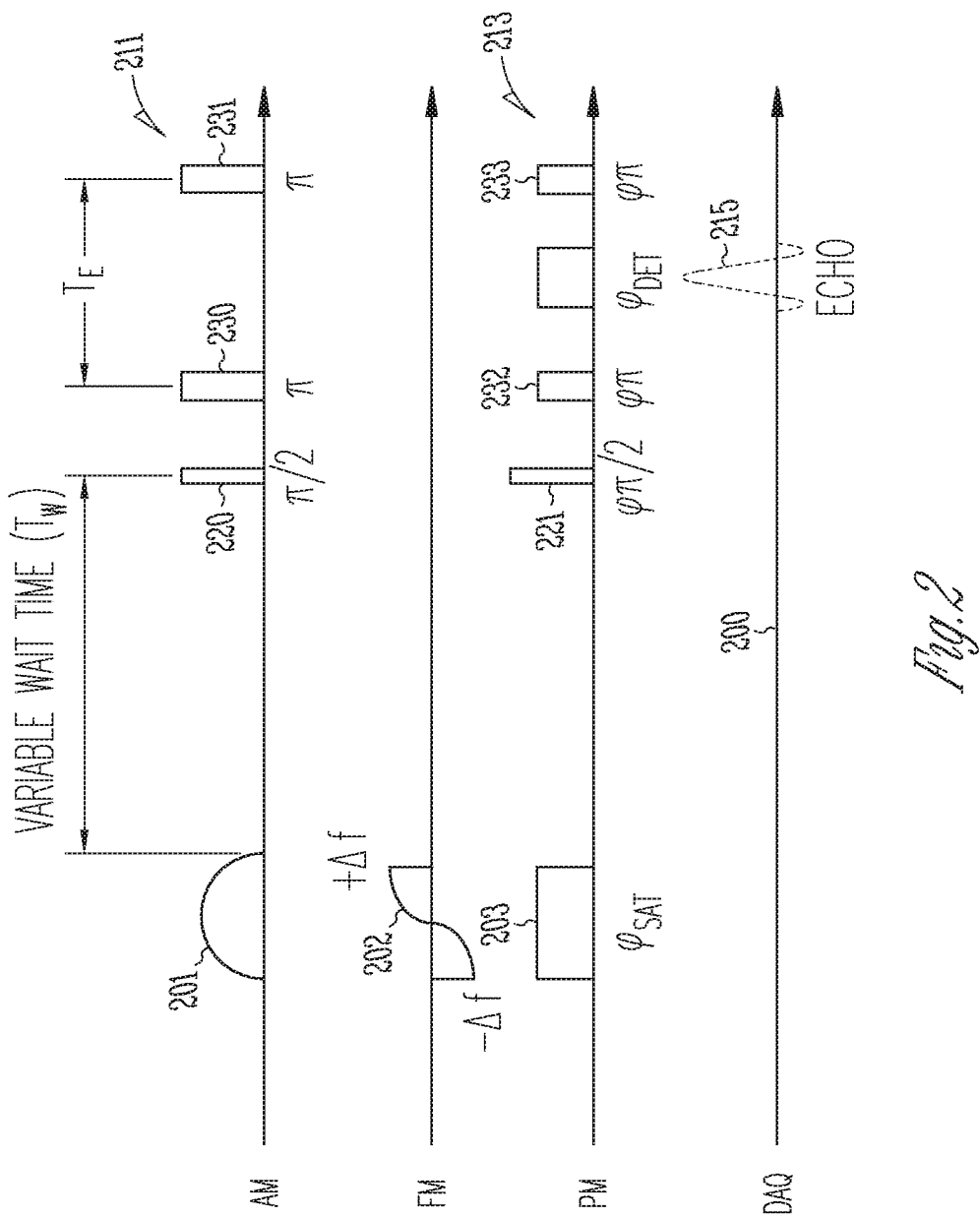
FIG. 2 is a plot of saturation pulses and readout pulses for transmission from the NMR tool, according to various examples of the disclosure.

FIG. 2 is a plot of saturation pulses and readout pulses for transmission from the NMR tool, according to various examples of the disclosure. For the purposes of brevity and clarity, the following discussion refers to the pulses 201-203 of FIG. 2 as saturation pulses. However, these pulses 201-203 may be implemented as either saturation pulses or inversion pulses.

The plot of FIG. 2 illustrates a single or a plurality of saturation pulses that may use various modulations 201-203 and their respective readout sequences 211, 213 that may be transmitted by the NMR tool 100. As described subsequently, FIG. 2 also illustrates a resulting data acquisition line 200 (DAQ) comprising an echo signal 215 that may be received by the NMR tool 100 as a result of the readout pulse sequences 211, 213. The saturation pulses 201-203 and readout pulses 211, 213 are for purposes of illustration only. Other examples may include many different implementations of these pulses.

In the example of FIG. 2, the saturation pulse may be realized by one or more of an AM pulse 201, an FM pulse 202, and/or a PM pulse 203 transmitted by the NMR tool 100. The AM pulse 201 and/or the FM pulse 202 may also be realized by transmission of just the PM pulse 203.

The saturation pulse 201-203 includes a pulse or a train of pulses that saturate or invert the polarized $M_z$ magnetization and readout sequence (e.g., Carr-Purcell-Meiboom-Gill (CPMG) where the nuclear spins are first flipped to a plane perpendicular to the static magnetic field direction using a tipping pulse followed by a series of refocusing pulses). For example, the fluid in a formation may be in a state of equilibrium. The saturation pulse 201-203 destroys that state of equilibrium, and the time it takes for the fluid to return to the state of equilibrium may be expressed as the $T_1$ time.

One or more of the pulse parameters (e.g., bandwidth, selectivity, pulse length, total RF energy consumption amplitude and duration) may be adjusted for one or more of the pulses 201-203 in order to optimize that particular saturation pulse in order to create a null state (i.e., zero nuclear spin state) in a reservoir of a formation. At the end of a saturation pulse or train of pulses, the $M_z$ magnetization becomes zero within the bandwidth while the $M_x$ and $M_y$ magnetization are non-zero—the resulting nuclear spin states are dependent on the type of modulation (e.g., AM, FM and PM) used for the saturation or inversion pulse.

The saturation pulse, once optimized for the formation, creates a broadband region in the formation that is in an initial, known state (i.e., null or zero spin state). A broadband RF pulse may be defined as a pulse that produces a wide range of spin isochromat components within the volume of interest (e.g., fluid) uniformly responding to the RF pulse. Such a broadband, highly volume-selective RF pulse may enable measurements of a well-defined section of fluid sample with minimal disturbance of the spins that are located outside of the section.

Various examples may vary the phase of the saturation pulse 201-203, the phases of the readout pulses 211, 213, the direction of the FM in a saturation pulse 201-203, and/or the wait time $T_w$ in order to reduce undesirable signal contributions. For example, the phase of the saturation pulse 201-203 may be selected from ($\varphi_{sat}$={0, 90, 180, 270} degrees; the direction of FM may be selected from a positive direction (i.e., {$-\Delta f$ to $+\Delta f$}) or a negative direction, (i.e., {$+\Delta f$ to $-\Delta f$}); the phase of the $\pi/2$ pulse 220, 221 and the phase of $\pi$ pulses 230-233 may be selected from {0, 90, 180, 270}; the variable wait time $T_w$ may be selected in a range from approximately 0.5 millisecond (ms)) to approximately 15000 ms.

An NMR signal 215 (i.e., echo) is detected by using a pulse sequence, such as CPMG, after the predetermined wait time $T_w$. A $\pi/2$ pulse 220, 221 from a monochromatic RF signal in readout sequence is calibrated for the on-resonance component of the magnetization to be rotated by 90 degrees around the axis as defined by the phase of the $\pi/2$ pulse. However, since the net rotation of any off-resonance components is not equal to 90 degrees, the off-resonance $M_x$ and $M_y$ components originated from the saturation pulse 201-203 may induce an undesirable signal within the data acquisition window. This may especially be true for NMR logging tools where spins are in the presence of significant gradient magnetic field. Since $M_x$ and $M_y$ states are dependent on the wait time $T_w$, and the modulation functions of the saturation pulse (i.e., direction of frequency modulation and phase of the saturation pulse) proper phase-cycling and the wait time $T_w$ may be used to reduce the signal contribution from this undesirable coherence. This may improve the signal averaging, thus improving the SNR per unit time.

Figure 3:
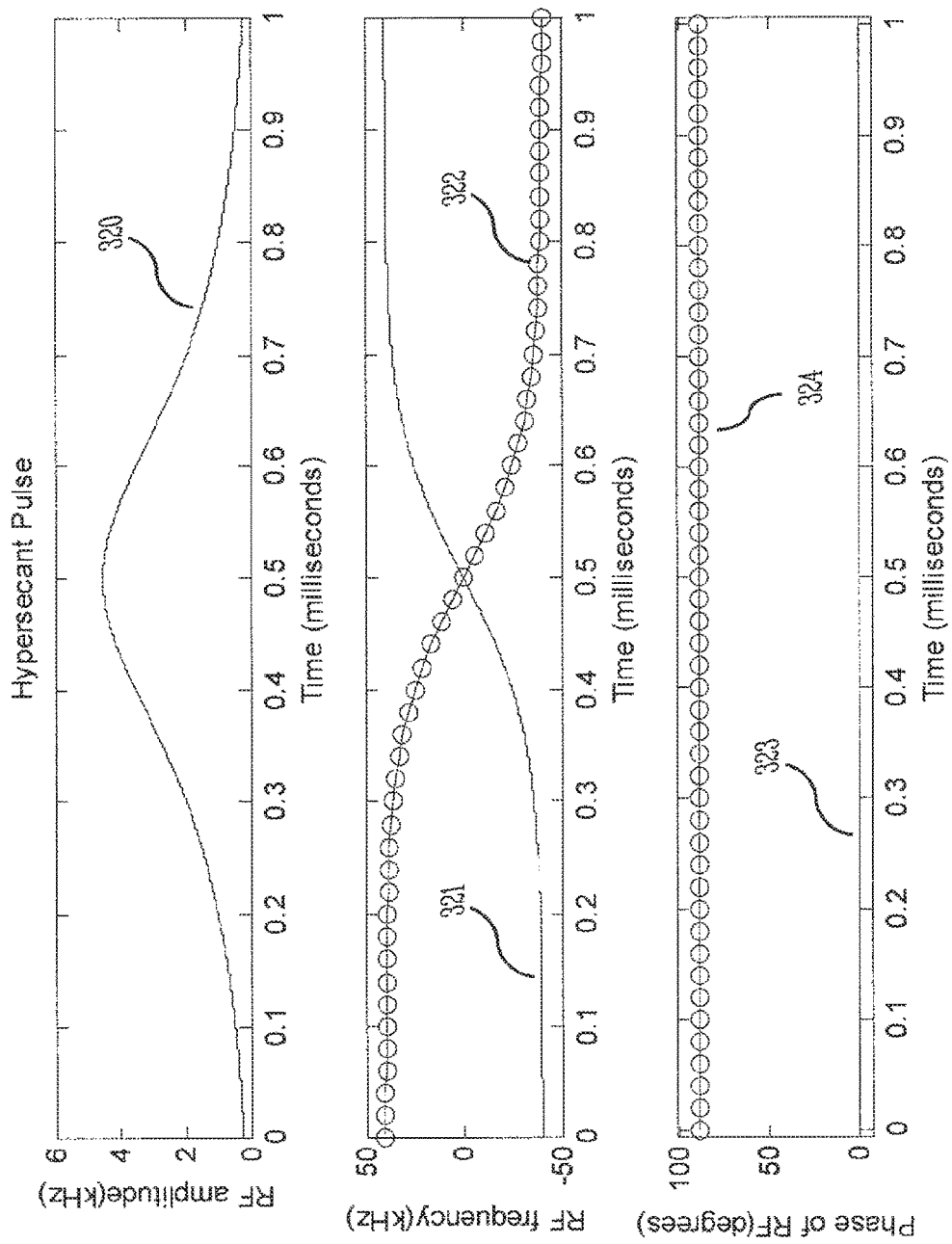
FIG. 3 is a plot of a representative modulation scheme of the saturation pulse, according to various examples of the disclosure.

FIG. 3 is a plot of a representative modulation scheme of the saturation pulse signals, according to various examples of the disclosure. The modulation scheme illustrated in FIG. 3 is a hyperbolic secant (HS) function modulated adiabatic pulse. This modulation scheme is for purposes of illustration only as other types of modulation may be used.

The modulated pulse of FIG. 3, when transmitted into a geological formation, may produce the saturation or inversion of the polarized nuclear spins. Depending on the various limiting factors such as peak RF power, total RF energy consumption, frequency selectivity, bandwidth, and/or pulse time, the optimized saturation pulse that produces the polarized nuclear spins may be determined by using various modulation functions for AM, FM and/or PM modulations.

In one example, curve 320 shows the modulation function for the amplitude modulation of the HS adiabatic pulse. Curves 321 and 322 show the modulation function for frequency modulation, with positive modulation direction (curve 321) and negative modulation direction (curve 322), of the HS adiabatic pulse. The HS adiabatic pulse realizes substantially uniform saturation of the $M_z$ magnetization over a wide bandwidth that is determined by a range of frequency sweep. Curve 323 and curve 324 show the phase of the saturation pulse. This phase cycling scheme is for purposes of illustration only as other types of phase cycling may be used.

Figure 4:
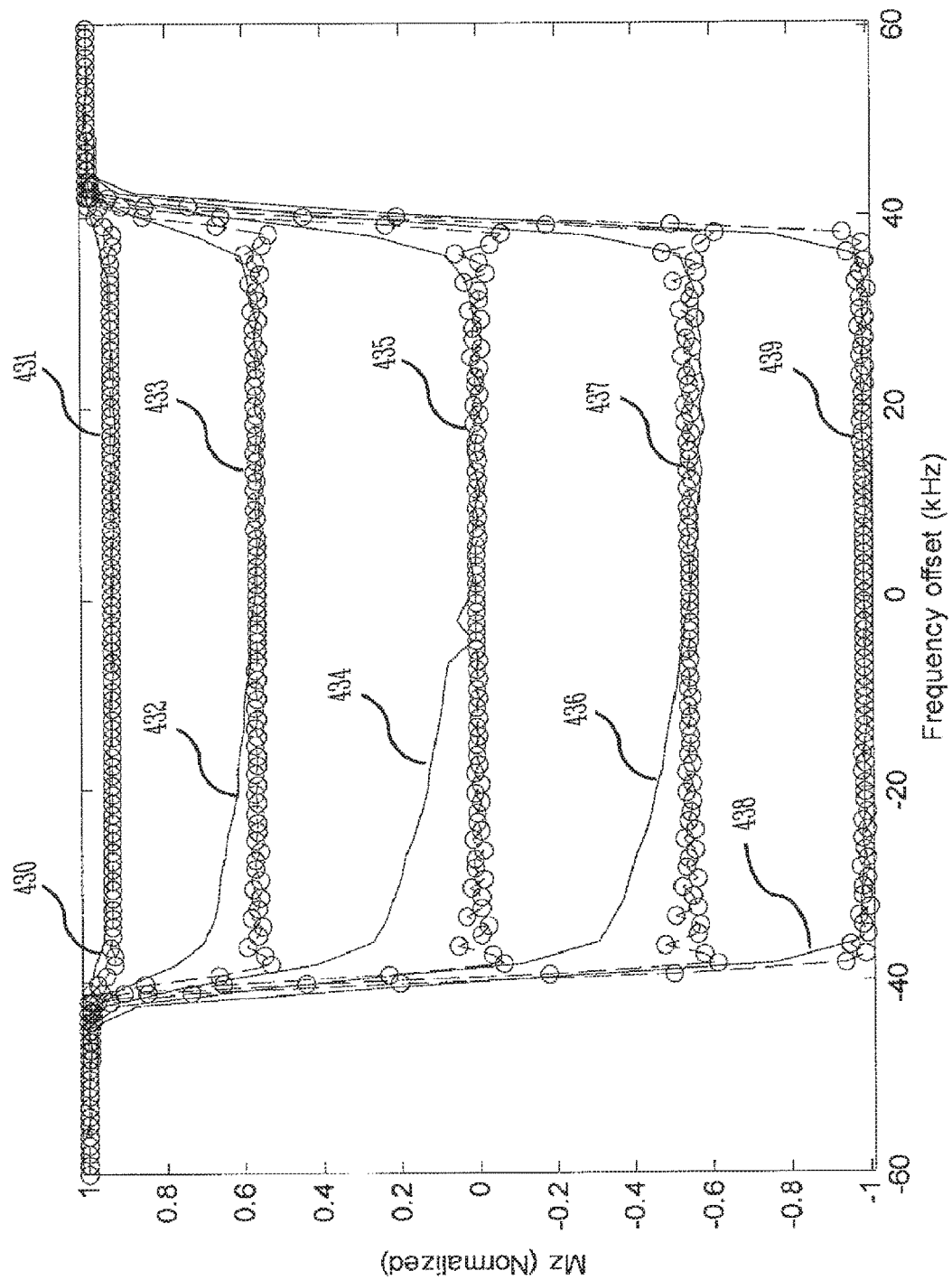
FIG. 4 is a plot of simulation and experimentation results of resultant $M_z$ magnetization resulting from the saturation pulse signals, according to various examples of the disclosure.

FIG. 4 is a plot of simulation and experimentation results of resultant $M_z$ magnetization resulting from the saturation pulse, according to various examples of the disclosure. The plotted results show the resultant $M_z$ magnetization, kilohertz (kHz), of proton spins measured shortly after the HS adiabatic pulse (see FIG. 3) at various $B_1$ amplitudes (i.e., RF peak). The simulation results are illustrated by the plots having dashed lines with circles and the experimental results are illustrated by the plots with solid lines.

Curves 430 and 431 illustrate the normalized $M_z$ magnetizations of nuclear spins after the HS adiabatic pulse with $B_1$ (i.e. RF peak amplitude) of 1.0 kHz. Curves 432 and 433 illustrate the normalized $M_z$ magnetizations of nuclear spins after the HS adiabatic pulse with $B_1$ (i.e. RF peak amplitude) of 2.7 kHz. Curves 434 and 435 illustrate the normalized $M_z$ magnetizations of nuclear spins after the HS adiabatic pulse with $B_1$ (i.e. RF peak amplitude) of 4.5 kHz. Curves 436 and 437 illustrate the normalized $M_z$ magnetizations of spins after the HS adiabatic pulse with $B_1$ (i.e. RF peak amplitude) of 6.6 kHz. Curves 438 and 439 illustrate the normalized $M_z$ magnetizations of spins after the HS adiabatic pulse with $B_1$ (i.e. RF peak amplitude) of 12.2 kHz.

The curves 430-439 illustrated in FIG. 4 show that the effective bandwidth of the pulse is about 80 kHz, which agrees with the range of the FM pulse, defined in the HS adiabatic pulse shown in FIG. 3. The curves 430-439 of FIG. 4 show that the responses of the spins are substantially uniform over the bandwidth. Slopes appearing in the experimental data (i.e., curves 430, 432, 434 and 436) are due to instrument artifacts. The curves 430-439 show that the HS adiabatic pulse has high selectivity, such that $M_z$ magnetizations outside of the bandwidth of the pulse is not perturbed by the HS adiabatic pulse, and a sharp transition between the perturbed spins and unperturbed spins is created.

Figure 5:
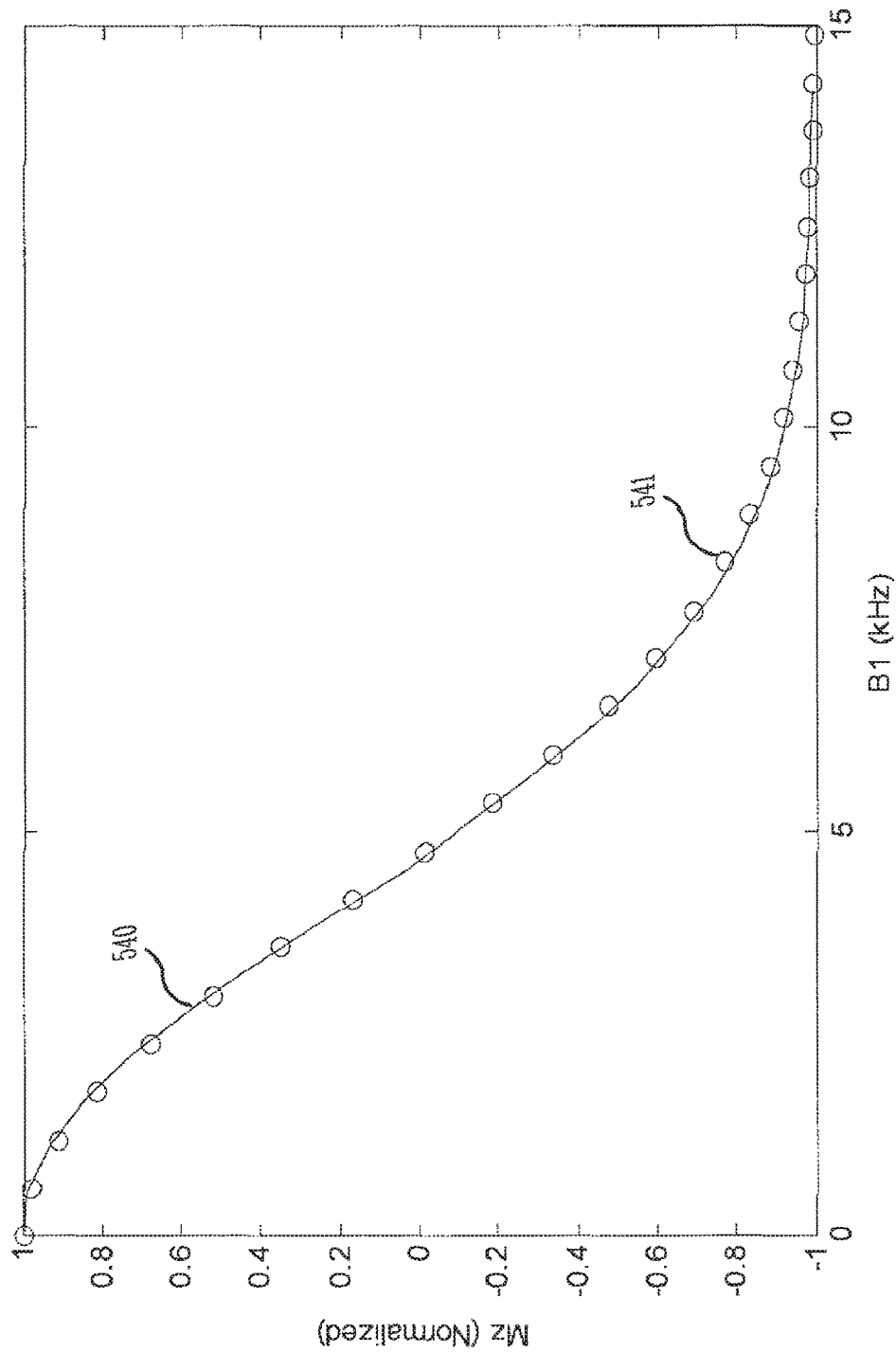
FIG. 5 is a plot of simulation and experimentation results of the $M_z$ magnetization as a function of peak RF amplitude, according to various examples of the disclosure.

FIG. 5 is a plot of simulation and experimentation results of the $M_z$ magnetization as a function of peak RF amplitude, according to various examples of the disclosure. This plot shows the response of the nuclear spin as a function of amplitude of the saturation pulse. In this example, the simulation results are indicated by circles (i.e., curve 541) while the experimental results are indicated by a line (i.e., curve 540). These plots show the $M_z$ magnetization as a function of the peak RF amplitude after the HS adiabatic pulse.

The coincident curves 540, 541 show that there is a match between the experimental data and the simulation data. This confirms that the optimal peak amplitude of an adiabatic saturation pulse may be theoretically found by solving the Bloch's equations for given parameters, such as duration of the RF pulse, range of the frequency sweep, functional forms of the AM, FM or PM.

In a conventional method, time-consuming calibration procedures are used to find an optimal amplitude of the saturation pulse that may nullify or invert the $M_z$ magnetization. For example, in one conventional implementation, the optimal amplitude of the saturation pulse is theoretically found for a given modulation function. Then, after calibration of the readout sequence (e.g., CPMG sequence to optimize the peak RF amplitude for the NMR signal detection), the optimal peak RF amplitude of the saturation/inversion pulse is analytically determined from the proportionality that is found from the Bloch's equation solution for a given adiabatic pulse.

Figure 6:
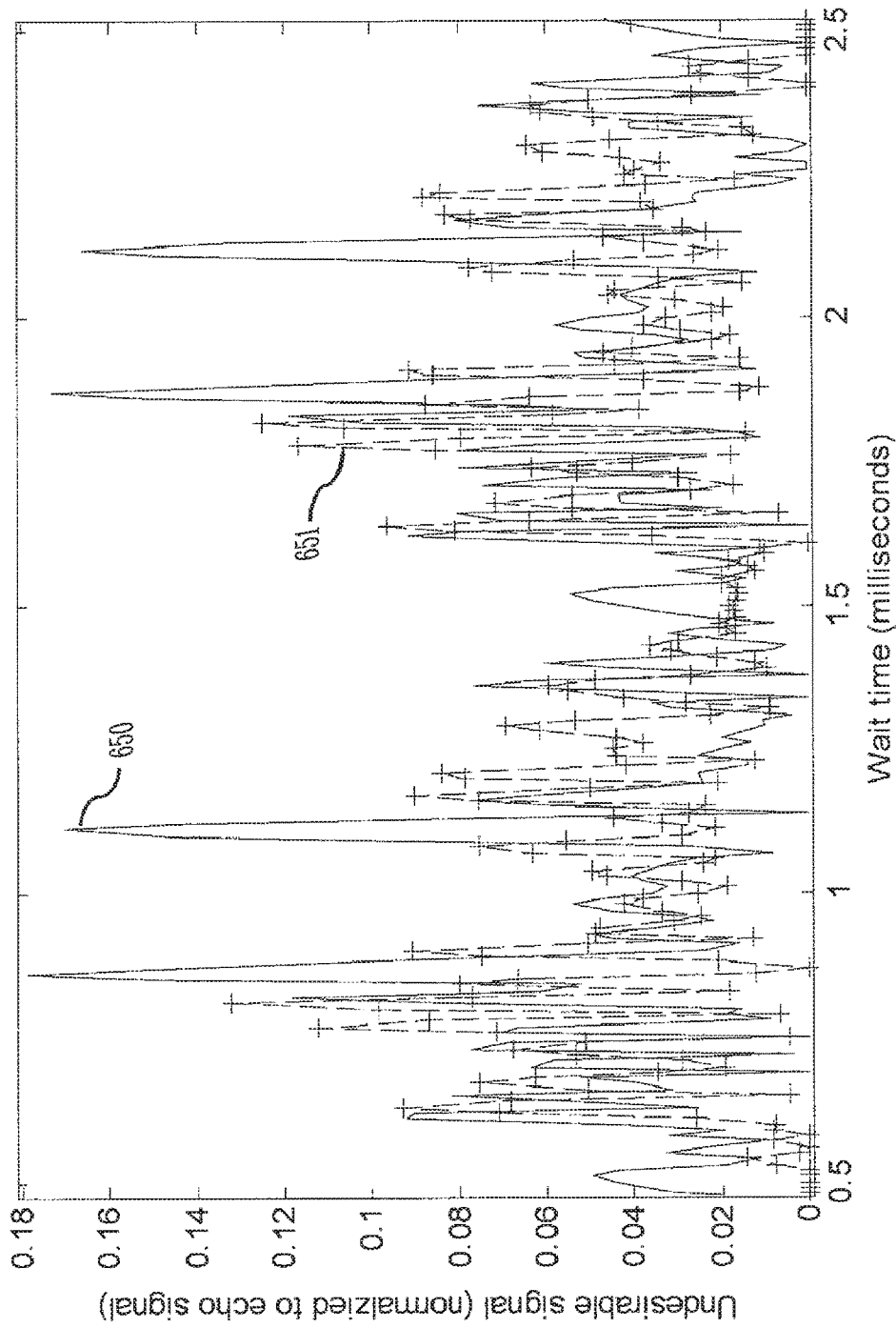
FIG. 6 is a plot of simulation results of an undesirable signal originating from the $M_x$, $M_y$ components after the saturation pulse, according to various examples of the disclosure.

FIG. 6 is a plot of simulation results of an undesirable signal originating from the $M_x$, $M_y$ components after the saturation pulse, according to various examples of the disclosure. These plots have been normalized to the maximum echo signal in the absence of the saturation pulse. The plots originated from the $M_x$, $M_y$ components after the HS saturation pulse, as a function of the wait time $T_w$, detected by the readout sequence within the data acquisition window.

Curve 650 (marked as a line) shows the simulation results of the undesirable signal when the phase of the saturation pulse and the readout pulse are composed of $$AM_{270} - FM_p - \left(\frac{\pi}{2}\right)_{270} - \pi_0,$$

where subscript 'p' represents the positive direction of the FM in the saturation pulse and subscripts '270' and '0' represent the phase of their respective pulses.

Curve 651 (marked as dashed line with crosses) shows the simulation results of the undesirable signal when the phase of the saturation pulse and the readout pulse are composed of $$AM_0 - FM_n - \left(\frac{\pi}{2}\right)_{270} - \pi_0,$$

where subscript 'n' represents the negative direction of the FM in the saturation pulse and subscripts '270' and '0' represent the phase of the respective pulse.

The plots 650, 651 of FIG. 6 show that the undesirable signal depends on the phase of the saturation pulse and the direction of the frequency modulation. It also shows that the undesirable signal depends on the variable wait time $T_w$. In one implementation, phase-cycling combination and appropriate wait times are selected such that the undesirable noise signal detected within the data acquisition window in the readout sequence is effectively suppressed. This may improve the signal-to-noise ratio (SNR) per unit time in some examples.

Figure 7:
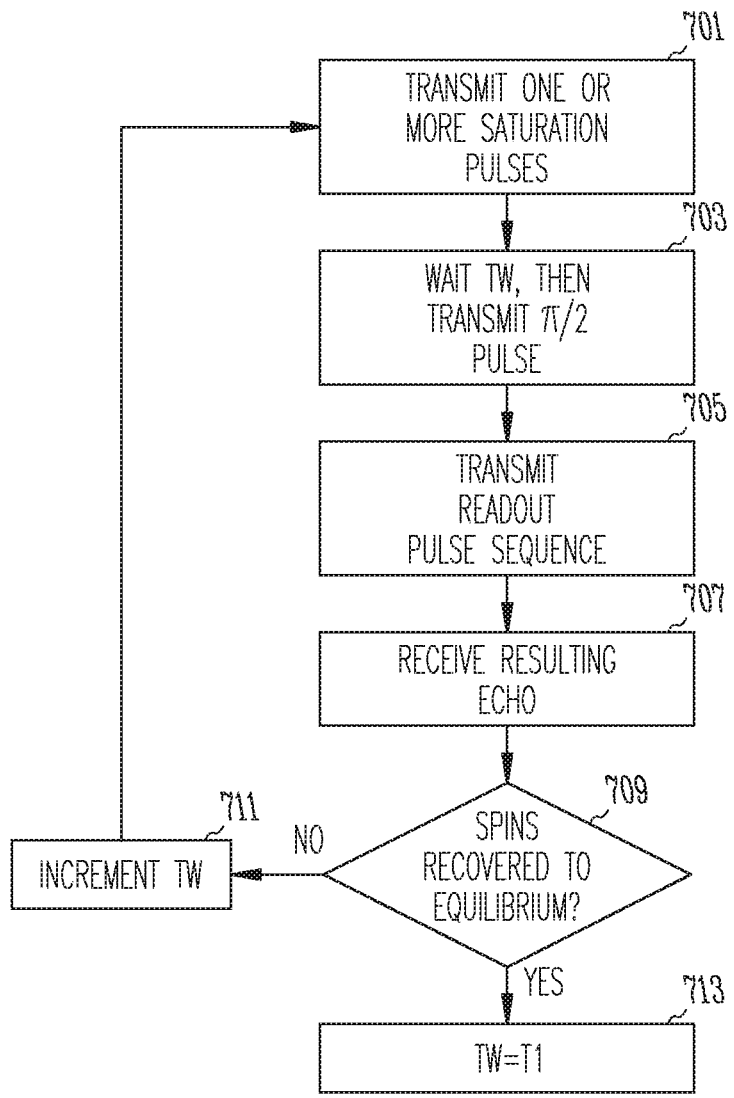
FIG. 7 is a flowchart of a method for shaping of an adiabatic saturation pulse, according to various examples of the disclosure.

FIG. 7 is a flowchart of a method for shaping of an adiabatic saturation pulse, according to various examples of the disclosure. This method may be used to generate an optimal adiabatic saturation pulse or pulses, by adjusting one or more of shape, amplitude, phase, or frequency of the adiabatic pulse, such that a substantially uniform response is received from the formation while using a minimum amount of RF energy, as defined by the Bloch's equations. Reference is made to the pulse plots of FIG. 2 in the description of this method. This method may be performed in a simulation, in a downhole environment, or a combination of a simulation and downhole. For example, the pulses may be transmitted into a geological formation by the NMR tool 100 and an echo received from the formation by the NMR tool 100, the transmission of pulses and receipt of the echo may be performed as a simulation, or the transmission of the pulses and receipt of the echo may a simulation for one or more initial executions of the method and then subsequent executions performed in a downhole environment.

In block 701, one or more configured adiabatic saturation pulses 201-203 are transmitted in order to measure the characteristics of an object (e.g., fluid). In block 703, after a first predetermined wait time $T_w$, a $$\frac{\pi}{2}$$

pulse 220, 221 (e.g., $$\frac{\pi}{2},$$

whose phase is defined by $$\varphi\frac{\pi}{2})$$

is transmitted in order to transition the nuclear spins from the $M_z$ plane to the $M_x$ and $M_y$ plane. In block 705, a recovery pulse sequence 230, 232 (e.g., $\pi$, whose phase is defined by $\varphi_\pi$) is then transmitted. In block 707, a resulting echo 215 is then received. In block 709, it may then be determined from the received echo whether, or to what percentage, the nuclear spins have recovered to equilibrium. In block 711, if the spins have not recovered to equilibrium, the variable wait time $T_w$ is incremented and the process is repeated until the nuclear spins have recovered to equilibrium. In block 715, the wait time $T_w$ is now equal to the $T_1$ relaxation time and, thus, an indication of the characteristics of the formation fluid.

Figure 8:
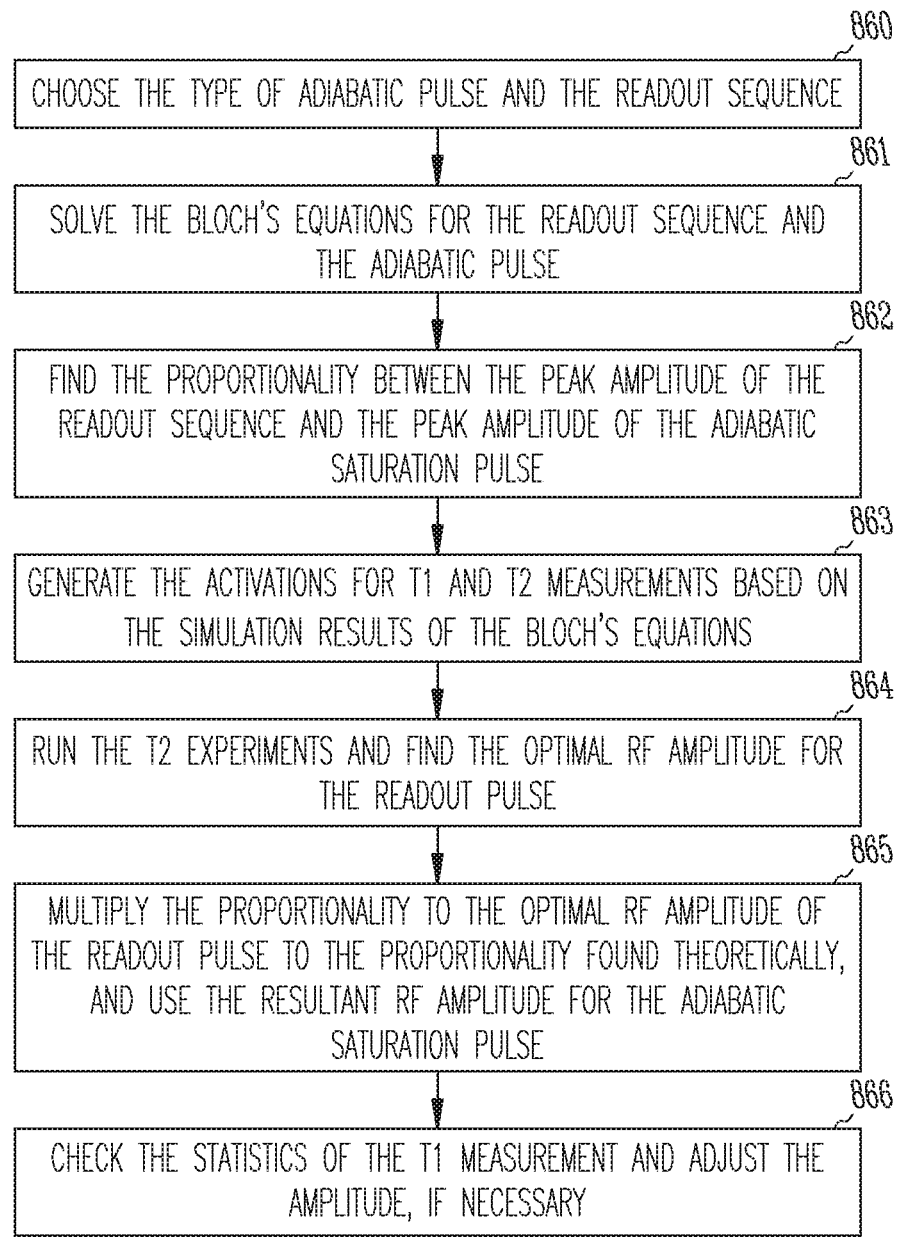
FIG. 8 is a flowchart of a method for saturation pulse calibration, according to various examples of the disclosure.

FIG. 8 is a flowchart of a method for calibration of the saturation pulses, according to various examples of the disclosure. Such a calibration method may be used to improve calibration of the adjustment of the pulse parameters for the saturation pulses in order to shape the pulse for transmission.

In block 860, a type of adiabatic saturation pulse and its associated readout pulse sequence is chosen. For an initial execution of the calibration procedure without any initial measurement data on which to base a selection, the adiabatic saturation pulse and associated readout pulse sequence may be chosen based on theoretical assignment. A choice of adiabatic pulse with a pulse length, shape and/or type of modulation can be performed according to the goal of the optimization. For example, one type of pulse may use a smaller RF peak amplitude or another type of pulse may use less RF energy. Thus, the initial pulse may be selected according to the optimization goal.

In block 861, Bloch's equations are solved for the readout sequence and the adiabatic saturation pulse in order to determine a desired amplitude for the pulse given the pulse shape. In block 862, the proportionality between the peak amplitude of the readout pulse sequence and the peak amplitude of the adiabatic saturation pulse is determined. In block 863, activations for $T_1$ and $T_2$ measurements, based on the simulation results of the Bloch's equations from block 861, are determined. In block 864, $T_2$ experiments are executed to find the optimal RF amplitude for the readout pulse sequence. In block 865, the proportionality to the optimal RF amplitude of the readout pulse sequence is multiplied with the proportionality found theoretically as discussed subsequently. The resultant RF amplitude is then used for the adiabatic saturation pulse. In block 866, the statistics of the $T_1$ measurement may then be checked and the amplitude adjusted if desired.

In determining the proportionality theoretically, a readout sequence may be selected from a single spin echo sequence or a CPMG sequence where a train of $\pi$ pulses are applied, and a train of echoes are detected from each $\pi$ pulse. Once the readout sequence is selected, in a first step, pulse parameters such as shape or pulse length can be selected. In a second step, with the selected readout pulse, an evolution of spins may be found by solving the Bloch's equations. By adjusting the strength of the time-varying magnetic field (B1), which is often expressed in kHz, one can find the optimal B1 field strength of the readout pulse sequence. In a third step, the adiabatic pulse may then be introduced to achieve saturation or inversion for given pulse parameters, such as modulation type, modulation function, pulse length, and phase. The Bloch's equations may then be solved to find the optimal B1 amplitude of the selected adiabatic pulse in order to achieve saturation or inversion of the nuclear spins. This optimal B1 is often expressed in kHz.

In a fourth step, the following expression may be executed: A:B=C:D, where A is the optimal B1 amplitude of the readout sequence found in the second step and B is the optimal B1 amplitude of the adiabatic pulse determined in the third step. In a fifth step, T2 experiments may be run using the pulse parameters that were selected in the first and second steps. In a sixth step, the RF amplitude (often expressed as kV) of the NMR logging tool may be adjusted to achieve a maximum echo signal for a given readout pulse sequence. An optimal RF voltage for the readout sequence may be assigned as 'C' in the expression in the fourth step.

In a seventh step, the optimal RF voltage for the choice of adiabatic pulse may be found from the above expression (i.e., C=(B/A)*C). For example, if A=10 kHz, B=3 kHz, C=1.2 kV, then, D=0.36 kV. In this example, the proportionality is B/A (i.e., 0.3). In an eighth step, the T1 experiments are executed using the choice of adiabatic pulse minimum wait time (TW) between the adiabatic pulse and the readout sequence, and the statistics checked to determine if it gives the minimum signal from the readout signal.

Figure 9:
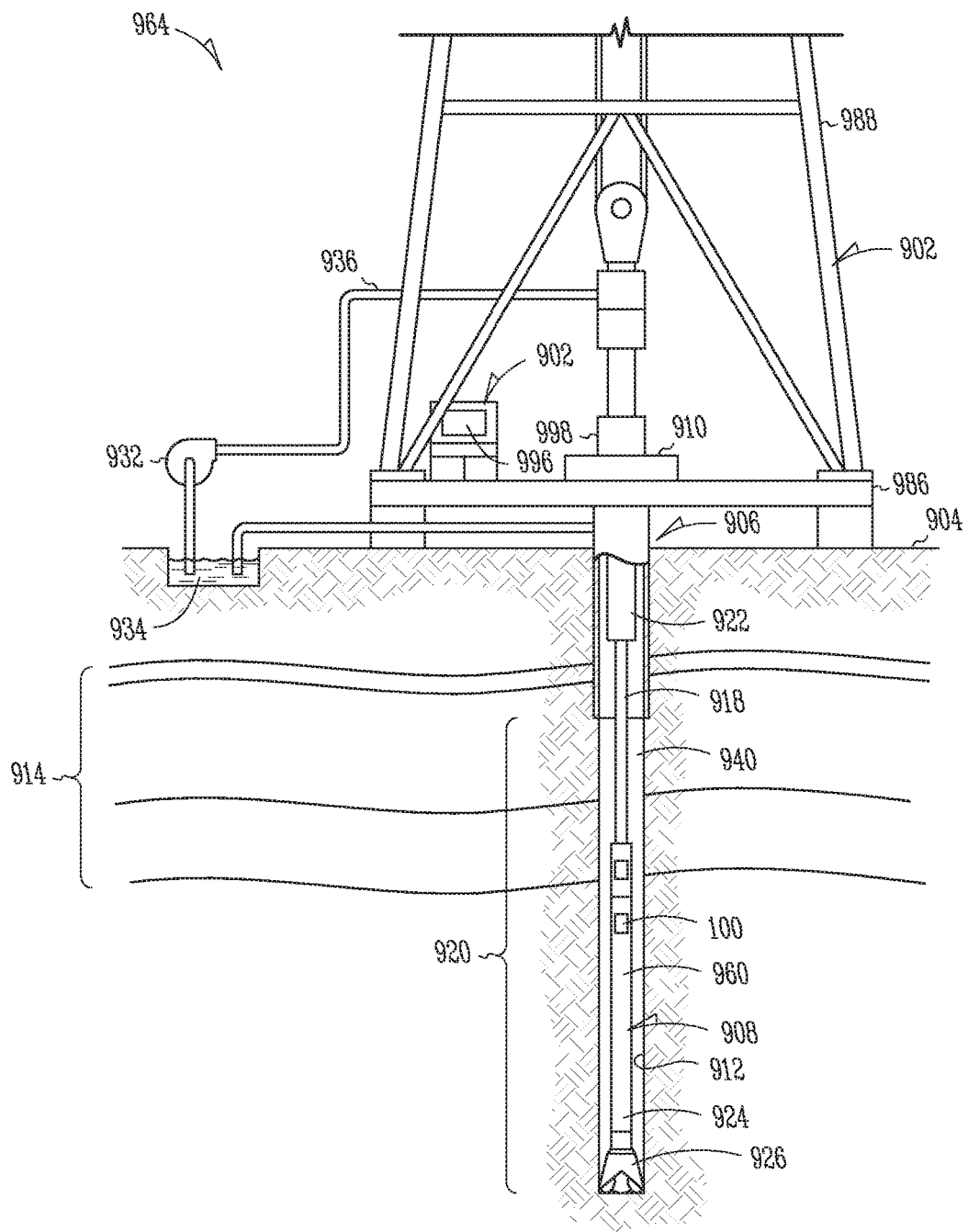
FIG. 9 is a diagram showing a drilling system, according to various examples of the disclosure.

FIG. 9 is a diagram showing a drilling system 964, according to various examples of the disclosure. The system 964 includes a drilling rig 902 located at the surface 904 of a well 906. The drilling rig 902 may provide support for a drillstring 908. The drillstring 908 may operate to penetrate the rotary table 910 for drilling the borehole 912 through the subsurface formations 914. The drillstring 908 may include a drill pipe 918 and a bottom hole assembly (BHA) 920 (e.g., drill string), perhaps located at the lower portion of the drill pipe 918.

The BHA 920 may include a measurement while drilling (MWD) or LWD tool 960, including the NMR tool 100, and a drill bit 926. The drill bit 926 may operate to create the borehole 912 by penetrating the surface 904 and the subsurface formations 914. The NMR tool 100 may be used to determine a condition of pipes that are located in the borehole 912 as described previously.

During drilling operations within the borehole 912, the drillstring 908 (perhaps including the drill pipe 918 and the BHA 920) may be rotated by the rotary table 910 and/or by the mud motor 990 that is located down hole. The drill collars 922 may be used to add weight to the drill bit 926. Drill collars 922 may also operate to stiffen the BHA 920, allowing the BHA 920 to transfer the added weight to the drill bit 926, and in turn, to assist the drill bit 926 in penetrating the surface 904 and subsurface formations 914.

During drilling operations within the borehole 912, a mud pump 932 may pump drilling fluid (sometimes referred to as "drilling mud") from a mud pit 934 through a hose 936 into the drill pipe 918 and down to the drill bit 926. The drilling fluid can flow out from the drill bit 926 and be returned to the surface 904 through an annular area 940 between the drill pipe 918 and the sides of the borehole 912. The drilling fluid may then be returned to the mud pit 934, where such fluid is filtered. In some examples, the drilling fluid can be used to cool the drill bit 926, as well as to provide lubrication for the drill bit 926 during drilling operations. Additionally, the drilling fluid may be used to remove subsurface formation cuttings created by operating the drill bit 926.

A workstation 992 including a controller 996 may include modules comprising hardware circuitry, a processor, and/or memory circuits that may store software program modules and objects, and/or firmware, and combinations thereof that are configured to execute the above-described methods of FIGS. 7 and 8 as instructions.

In an example, the NMR tool 100 may be used to transmit an electromagnetic field and then measure the resulting secondary electromagnetic field responses generated by the pipes being inspected. The resulting data may be transmitted to the surface workstation 992 via telemetry. The workstation 992, with its controller 996, may process that telemetry, execute any methods disclosed herein, and generate a two-dimensional image of the downhole pipes.

Figure 10:
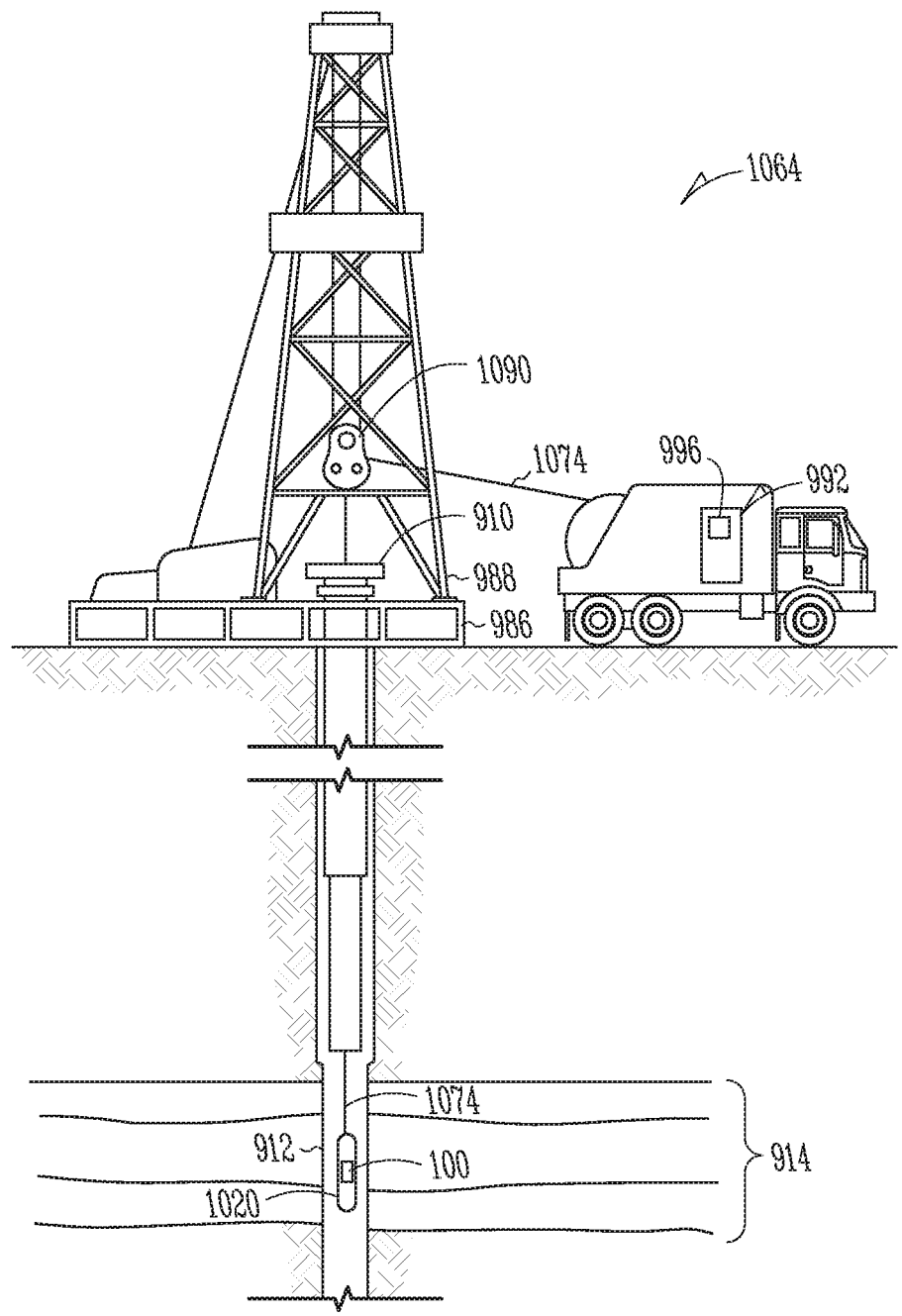
FIG. 10 is a diagram showing a wireline system, according to various examples of the disclosure.

FIG. 10 is a diagram showing a wireline system 1064, according to various examples of the disclosure. The system 1064 may comprise at least one wireline logging tool body 1020, as part of a wireline logging operation in a borehole 912, including the NMR tool 100 as described previously.

A drilling platform 986 equipped with a derrick 988 that supports a hoist 1090 can be seen. Drilling oil and gas wells is commonly carried out using a string of drill pipes connected together so as to form a drillstring that is lowered through a rotary table 910 into the borehole 912. Here it is assumed that the drillstring has been temporarily removed from the borehole 912 to allow the wireline logging tool body 1020, such as a probe or sonde with the inspection tool 100, to be lowered by wireline or logging cable 1074 (e.g., slickline cable) into the borehole 912. Typically, the wireline logging tool body 1020 is lowered to the bottom of the region of interest and subsequently pulled upward at a substantially constant speed.

During the upward trip, at a series of depths, the NMR tool 100 may be used to determine the characteristics of the formation 914 or a reservoir in the formation 914. The resulting data may be communicated to a surface logging facility (e.g., workstation 992) for processing, analysis, and/or storage. The workstation 992 may have a controller 996 that is able to execute any methods disclosed herein.

Figure 11:
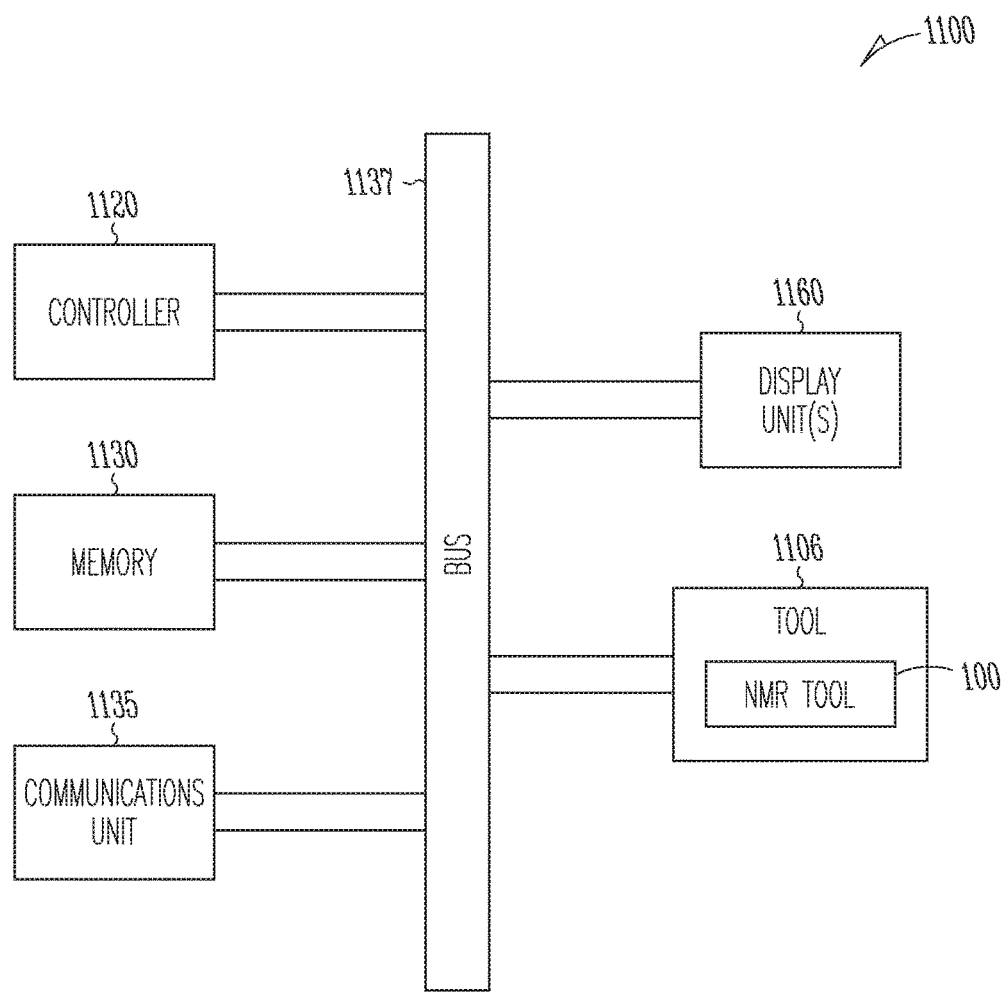
FIG. 11 is a block diagram of an example system operable to implement the activities of multiple methods, according to various examples of the disclosure.

FIG. 11 is a block diagram of an example system 1100 operable to implement the activities of multiple methods, according to various examples of the disclosure. The system 1100 may include a tool housing 1106 having the NMR tool 100 disposed therein. The system 1100 may be implemented as shown in FIGS. 9 and 10 with reference to the workstation 992 and controller 996.

The system 1100 may include circuitry such as a controller 1120, a memory 130, and a communications unit 1135. The memory 1130 may be structured to include a database. The controller 1120, the memory 1130, and the communications unit 1135 may be arranged to operate as control circuitry to control operation of the NMR tool 100 and execute any methods disclosed herein in order to determine the characteristics of a fluid and/or formation.

The communications unit 1135 may include communications capability for communicating from downhole to the surface or from the surface to downhole. Such communications capability can include a telemetry system such as mud pulse telemetry. In another example, the communications unit 1135 may use combinations of wired communication technologies and wireless technologies.

The system 1100 may also include a bus 1137 that provides electrical conductivity among the components of the system 1100. The bus 1137 can include an address bus, a data bus, and a control bus, each independently configured or in an integrated format. The bus 1137 may be realized using a number of different communication mediums that allows for the distribution of components of the system 1100. The bus 1137 may include a network. Use of the bus 1137 may be regulated by the controller 1120.

The system 1100 may include display unit(s) 1160 as a distributed component on the surface of a wellbore, which may be used with instructions stored in the memory 1130 to implement a user interface to monitor the operation of the tool 1106 or components distributed within the system 1100. The user interface may be used to input parameter values for thresholds such that the system 1100 can operate autonomously substantially without user intervention in a variety of applications. The user interface may also provide for manual override and change of control of the system 1100 to a user. Such a user interface may be operated in conjunction with the communications unit 1135 and the bus 1137.

These implementations can include a machine-readable storage device having machine-executable instructions, such as a computer-readable storage device having computer-executable instructions. Further, a computer-readable storage device may be a physical device that stores data represented by a physical structure within the device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices.

Example 1 is a method for shaping a nuclear magnetic resonance (NMR) pulse, the method comprising adjusting one or more of a shape, an amplitude, a phase, or a frequency of an adiabatic pulse to produce a configured adiabatic pulse; generating the configured adiabatic pulse to transmit the configured adiabatic pulse into an object; and determining when the adiabatic pulse is configured to produce a substantially uniform saturation or inversion of magnetization from the object.

In Example 2, the subject matter of Example 1 can further include transmitting a readout pulse sequence a predetermined wait time after transmitting the configured adiabatic pulse into the object.

In Example 3, the subject matter of Example 3 can further include wherein generating the configured adiabatic pulse comprises generating a saturation pulse or an inversion pulse.

In Example 4, the subject matter of Examples 1-3 can further include wherein generating the configured adiabatic pulse comprises modulating the pulse with one or more of amplitude modulation, frequency modulation, or phase modulation.

In Example 5, the subject matter of Examples 1-4 can further include wherein generating the configured adiabatic pulse comprises modulating the pulse with a hyperbolic secant function.

In Example 6, the subject matter of Examples 1-5 can further include wherein determining when the adiabatic pulse is configured to produce a substantially uniform saturation or inversion response comprises determining the uniform saturation or inversion response based on a field gradient at a bandwidth.

In Example 7, the subject matter of Examples 1-6 can further include wherein determining when the adiabatic pulse is configured to produce a substantially uniform saturation or inversion response comprises determining a calculated response from Bloch's equations based on an echo response.

In Example 8, the subject matter of Examples 1-7 can further include: transmitting the configured adiabatic pulse into a fluid in a geological formation; waiting a predetermined time; transmitting a readout pulse sequence based on the pulse; receiving an echo from the fluid; determining from Bloch's equations if the echo indicates spin saturation or inversion; and determining characteristics of the fluid based on the predetermined wait time.

In Example 9, the subject matter of Examples 1-8 can further include wherein the predetermined wait time is substantially equal to T1 relaxation time.

Example 10 is a nuclear magnetic resonance (NMR) device, comprising an NMR unit to transmit and receive NMR signals; and control circuitry coupled to the NMR unit, the control circuitry to generate one or more adiabatic saturation or inversion pulses based on adjusted pulse parameters wherein the generated pulses produce a substantially uniform nuclear spin saturation or nuclear spin inversion response from a fluid.

In Example 11, the subject matter of Example 10 can further include wherein the generated pulse produces the substantially uniform nuclear spin saturation or nuclear spin inversion response at a least amount of total radio frequency (RF) energy as determined by Bloch's equations.

In Example 12, the subject matter of Examples 10-11 can further include wherein the pulse parameters comprise pulse shape, bandwidth, selectivity, length, phase, frequency, total radio frequency (RF) energy consumption, and amplitude.

In Example 13, the subject matter of Examples 10-12 can further include wherein the control circuitry is to wait a predetermined time prior to controlling transmission of a recovery pulse sequence and receiving an echo indicative of a percentage of nuclear spin saturation or nuclear spin inversion of the fluid.

In Example 14, the subject matter of Examples 10-13 can further include wherein the control circuitry is to determine the percentage of nuclear spin saturation or nuclear spin inversion of the fluid is based on the predetermined time.

In Example 15, the subject matter of Examples 10-14 can further include a $\pi/2$ pulse to transition the nuclear spins from a $M_z$ plane to a $M_x$ and $M_y$ spins from a Mz plane to a Mx and My plane.

Example 16 is a system for NMR logging, comprising: a downhole tool housing including a nuclear magnetic resonance (NMR) tool, the NMR tool comprising: an NMR unit comprising a transmitter to transmit NMR signals and a receiver to receive echoes from a formation in response to the transmitted NMR signals; and control circuitry coupled to the NMR unit, the control circuitry to shape an adiabatic pulse by adjusting pulse parameters such that the adiabatic pulse is configured to produce a substantially uniform nuclear spin saturation or nuclear spin inversion response from a fluid using a least amount of radio frequency (RF) energy as determined by Bloch's equations.

In Example 17, the subject matter of Example 16 can further include, wherein the NMR tool is disposed in a wireline tool.

In Example 18, the subject matter of Examples 16-17 can further include wherein the NMR tool is disposed in a drill string tool.

In Example 19, the subject matter of Examples 16-18 can further include wherein the control circuitry is to: select an adiabatic pulse and readout sequence from a plurality of adiabatic pulses and read out sequences; determine results for Bloch's equations for the selected adiabatic pulse and readout sequence; determine a first proportionality between a peak amplitude of the selected readout sequence and a peak amplitude of the selected adiabatic pulse; generate activations for T1 and T2 measurements based on the results of the Bloch's equations; determine an RF amplitude for a readout pulse of the readout sequence; and multiply the first proportionality by a second proportionality determined theoretically to generate a resultant RF amplitude for the adiabatic pulse.

In Example 20, the subject matter of Examples 16-19 can further include, wherein the controller is to select from the plurality of adiabatic pulses and read out sequences comprising AM pulses, FM pulses, or PM pulses.

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of ordinary skill in the art upon studying the above description.

What is claimed is:

1. A method for shaping a downhole nuclear magnetic resonance (NMR) pulse, the method comprising:
    adjusting one or more of a shape, an amplitude, a phase, or a frequency of an adiabatic pulse to produce a configured adiabatic pulse of saturation or inversion based on:
        total and peak radio frequency (RF);
        power consumption;
        pulse width; or
        bandwidth;
    generating the configured adiabatic pulse to transmit the configured adiabatic pulse into a downhole geological formation;
    determining when the adiabatic pulse is configured to produce a saturation or inversion of magnetization from the geological formation by determining a calculated response from Bloch's equations based on an echo response;
    transmitting the configured adiabatic pulse into a fluid in the geological formation;
    waiting a predetermined time;
    transmitting a readout pulse sequence based on the pulse;
    receiving an echo from the fluid;
    determining from Bloch's equations if the echo indicates spin saturation or inversion; and
    determining characteristics of the fluid based on the predetermined wait time.

2. The method of claim 1, further comprising transmitting a readout pulse sequence a predetermined wait time after transmitting the configured adiabatic pulse into the geological formation.

3. The method of claim 1, wherein generating the configured adiabatic pulse comprises generating a saturation pulse or an inversion pulse.

4. The method of claim 1, wherein generating the configured adiabatic pulse comprises modulating the pulse with one or more of amplitude modulation, frequency modulation, or phase modulation.

5. The method of claim 4, wherein generating the configured adiabatic pulse comprises modulating the pulse with a hyperbolic secant function.

6. The method of claim 5, wherein determining when the adiabatic pulse is configured to produce a saturation or inversion response comprises determining the saturation or inversion response based on a field gradient at a bandwidth.

7. The method of claim 1, wherein the predetermined wait time is equal to T1 relaxation time.

8. A nuclear magnetic resonance (NMR) device for downhole logging, comprising:
    an NMR unit to transmit and receive NMR signals; and
    control circuitry coupled to the NMR unit, the control circuitry configured to generate one or more adiabatic pulses of saturation or inversion based on:
        total and peak radio frequency (RF);
        power consumption;
        pulse width; or
        bandwidth,
    wherein the generated pulses produce a nuclear spin saturation or nuclear spin inversion response from a fluid of a downhole geological formation, and
    wherein the control circuitry is further configured to wait a predetermined time prior to controlling transmission of a recovery pulse sequence and receiving an echo indicative of a percentage of nuclear spin saturation or nuclear spin inversion of the fluid.

9. The NMR device of claim 8, wherein the generated pulse produces the nuclear spin saturation or nuclear spin inversion response at a least amount of total radio frequency (RF) energy as determined by Bloch's equations.

10. The NMR device of claim 8, wherein the pulse parameters comprise pulse shape, bandwidth, selectivity, length, phase, frequency, total radio frequency (RF) energy consumption, and amplitude.

11. The NMR device of claim 8, wherein the control circuitry is to determine the percentage of nuclear spin saturation or nuclear spin inversion of the fluid is based on the predetermined time.

12. The NMR device of claim 8, wherein the readout pulse sequence comprises a $\eta/2$ pulse to transition the nuclear spins from a Mz plane to a Mx and My plane.

13. A system for NMR logging, comprising:
    a downhole logging tool housing including a nuclear magnetic resonance (NMR) tool, the NMR tool comprising:
        an NMR unit comprising a transmitter to transmit NMR signals and a receiver to receive echoes from a formation in response to the transmitted NMR signals; and
        control circuitry coupled to the NMR unit, the control circuitry configured to shape an adiabatic pulse of saturation or inversion by adjusting:
            total and peak radio frequency (RF);
            power consumption;
            pulse width; or
            bandwidth,
        such that the adiabatic pulse is configured to produce a nuclear spin saturation or nuclear spin inversion response from a fluid of a downhole geological formation using a least amount of RF energy as determined by Bloch's equations, wherein the control circuitry is further configured to:
select an adiabatic pulse and readout sequence from a plurality of adiabatic pulses and read out sequences;
determine results for Bloch's equations for the selected adiabatic pulse and readout sequence;
determine a first proportionality between a peak amplitude of the selected readout sequence and a peak amplitude of the selected adiabatic pulse;
generate activations for T1 and T2 measurements based on the results of the Bloch's equations;
determine an RF amplitude for a readout pulse of the readout sequence; and
multiply the first proportionality by a second proportionality determined theoretically to generate a resultant RF amplitude for the adiabatic pulse.

14. The system of claim 13, wherein the NMR tool is disposed in a wireline tool.

15. The system of claim 13, wherein the NMR tool is disposed in a drill string tool.

16. The system of claim 13, wherein the controller is to select from the plurality of adiabatic pulses and read out sequences comprising AM pulses, FM pulses, or PM pulses.

* * * * *